United States Patent
Rees et al.

(10) Patent No.: US 11,452,990 B2
(45) Date of Patent: Sep. 27, 2022

(54) CATALYST AND PROCESS USING THE CATALYST FOR MANUFACTURING FLUORINATED HYDROCARBONS

(71) Applicant: MEXICHEM FLUOR S.A. DE C.V., San Luis Potosi (MX)

(72) Inventors: Claire Nicola Rees, Runcorn (GB); Claire Elizabeth McGuinness, Runcorn (GB); Andrew Paul Sharratt, Runchorn (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 58 days.

(21) Appl. No.: 16/331,450

(22) PCT Filed: Sep. 7, 2017

(86) PCT No.: PCT/GB2017/052616
§ 371 (c)(1),
(2) Date: Mar. 7, 2019

(87) PCT Pub. No.: WO2018/046927
PCT Pub. Date: Mar. 15, 2018

(65) Prior Publication Data
US 2020/0086299 A1    Mar. 19, 2020

(30) Foreign Application Priority Data
Sep. 7, 2016  (GB) .................................... 1615197

(51) Int. Cl.
*B01J 23/26*    (2006.01)
*B01J 23/06*    (2006.01)
(Continued)

(52) U.S. Cl.
CPC ............... *B01J 23/26* (2013.01); *B01J 23/06* (2013.01); *B01J 35/023* (2013.01);
(Continued)

(58) Field of Classification Search
None
See application file for complete search history.

(56) References Cited

U.S. PATENT DOCUMENTS

| | | |
|---|---|---|
| 231,840 A | 8/1886 | Neahous |
| 2,700,686 A | 1/1955 | Dickey et al. |
| 2,889,379 A | 6/1959 | Ruh et al. |
| 2,918,501 A | 12/1959 | Brehm et al. |
| 2,931,840 A | 4/1960 | Marquis |
| 2,996,555 A | 8/1961 | Rausch |
| 3,000,979 A | 9/1961 | Gibbs |
| 3,398,204 A | 8/1968 | Gallant |

(Continued)

FOREIGN PATENT DOCUMENTS

| | | |
|---|---|---|
| CN | 104475080 A | 4/2015 |
| CN | 105688890 | 6/2016 |

(Continued)

OTHER PUBLICATIONS

Burton et al., J. Fluorine Chem., 44(1), 1989; pp. 167-174.
(Continued)

*Primary Examiner* — Colin W. Slifka
(74) *Attorney, Agent, or Firm* — Crowell & Moring LLP

(57) ABSTRACT

A catalyst comprising one or more metal oxides, wherein the catalyst has a total pore volume equal to or greater than 0.3 cm³/g and a mean pore diameter greater than or equal to 90 Å, where in the pore volume is measured using $N_2$ adsorption porosimetry and the mean pore diameter is measured using $N_2$ BET adsorption porosimetry.

46 Claims, 6 Drawing Sheets

(51) Int. Cl.
  *B01J 35/02* (2006.01)
  *B01J 35/10* (2006.01)
  *B01J 37/08* (2006.01)
  *B01J 37/26* (2006.01)
  *C07C 17/087* (2006.01)
  *C07C 21/18* (2006.01)

(52) U.S. Cl.
  CPC ....... *B01J 35/1038* (2013.01); *B01J 35/1042* (2013.01); *B01J 35/1061* (2013.01); *B01J 37/08* (2013.01); *B01J 37/26* (2013.01); *C07C 17/087* (2013.01); *C07C 21/18* (2013.01)

(56) References Cited

U.S. PATENT DOCUMENTS

| | | |
|---|---|---|
| 3,674,665 A | 7/1972 | Cristol et al. |
| 3,739,036 A | 6/1973 | Valicenti et al. |
| 3,793,229 A | 2/1974 | Groppeli et al. |
| 4,093,670 A | 6/1978 | Ozawa et al. |
| 4,188,284 A | 2/1980 | Quick et al. |
| 4,220,608 A | 9/1980 | Feiring |
| 4,465,786 A | 8/1984 | Zimmer et al. |
| 4,798,818 A | 1/1989 | Baizer et al. |
| 5,672,803 A | 9/1997 | Smith et al. |
| 5,679,875 A | 10/1997 | Aoyama et al. |
| 5,763,711 A | 6/1998 | Ito |
| 5,811,603 A | 9/1998 | Eisheikh |
| 5,856,593 A | 1/1999 | Powell et al. |
| 5,986,151 A | 11/1999 | VanDerPuy |
| 6,111,150 A | 8/2000 | Sakyu et al. |
| 6,124,510 A | 9/2000 | Elsheikh et al. |
| 6,329,559 B1 | 12/2001 | Sievert et al. |
| 6,734,332 B1 | 5/2004 | Slaugh et al. |
| 2004/0049088 A1 | 3/2004 | Lacroix et al. |
| 2004/0167015 A1 | 8/2004 | Cann et al. |
| 2005/0038302 A1 | 2/2005 | Hedrick et al. |
| 2005/0090698 A1 | 4/2005 | Merkel et al. |
| 2005/0228202 A1 | 10/2005 | Nappa et al. |
| 2006/0122441 A1 | 6/2006 | Tung |
| 2006/0269484 A1 | 11/2006 | Knopeck et al. |
| 2007/0004585 A1 | 1/2007 | Amos et al. |
| 2007/0100175 A1 | 5/2007 | Miller et al. |
| 2007/0112230 A1 | 5/2007 | Mukhopadhyay et al. |
| 2007/0129579 A1 | 6/2007 | Wang et al. |
| 2007/0197842 A1 | 8/2007 | Mukhopadhyay et al. |
| 2008/0051611 A1 | 2/2008 | Wang et al. |
| 2009/0118554 A1 | 5/2009 | Rao et al. |
| 2009/0209792 A1* | 8/2009 | Sharratt ................. B01J 23/26 570/165 |
| 2010/0072415 A1 | 3/2010 | Rao et al. |
| 2010/0268002 A1 | 10/2010 | Nose et al. |
| 2011/0060111 A1 | 3/2011 | Cann et al. |
| 2011/0118513 A1 | 5/2011 | Smith et al. |
| 2011/0160497 A1 | 6/2011 | Deur-Bert et al. |
| 2013/0303812 A1 | 11/2013 | Birke et al. |

FOREIGN PATENT DOCUMENTS

| Country | Number | Date | |
|---|---|---|---|
| DE | 1140928 | 12/1962 | |
| DE | 2128341 | 12/1971 | |
| DE | 69406525 | 6/1995 | |
| EP | 0393517 A2 | 10/1990 | |
| EP | 0270006 | 2/1991 | |
| EP | 0436989 | 7/1991 | |
| EP | 0502605 | 9/1992 | |
| EP | 0644173 | 3/1995 | |
| EP | 0657408 A1 | 6/1995 | |
| EP | 0726243 | 8/1996 | |
| EP | 0773061 | 5/1997 | |
| EP | 0957074 | 11/1999 | |
| EP | 0752403 | 1/2001 | |
| EP | 0939071 | 7/2003 | |
| EP | 1350564 | 10/2003 | |
| EP | 1502906 | 2/2005 | |
| EP | 0957074 | 1/2006 | |
| EP | 1067106 | 4/2006 | |
| EP | 1900716 | 10/2012 | |
| EP | 1877181 | 6/2015 | |
| EP | 1877181 B1 | 6/2015 | |
| EP | 1918269 | 1/2019 | |
| EP | 3 330 244 B1 | 1/2020 | |
| FR | 2342952 | 9/1977 | |
| FR | 2740994 | 5/1997 | |
| GB | 1407696 | 9/1975 | |
| GB | 1415649 | 11/1975 | |
| GB | 2011463 A1 | 7/1979 | |
| GB | 2162082 | 1/1986 | |
| GB | 1615197.9 | 10/2016 | |
| JP | S54-116004 | 8/1979 | |
| JP | H02-280837 | 11/1990 | |
| JP | H04346948 | 12/1992 | |
| JP | 07-206728 | 8/1995 | |
| JP | H11140002 | 5/1999 | |
| JP | 2006-111611 A | 4/2006 | |
| JP | 2012-501826 | 1/2012 | |
| KR | 10-2011-0004431 | 1/2011 | |
| KR | 10-2011-0004434 | 1/2011 | |
| KR | 10-1343471 | 5/2011 | |
| KR | 10-1343618 | 5/2011 | |
| RU | 2322291 C1 | 4/2008 | |
| RU | 2402378 C1 | 10/2010 | |
| RU | 2431524 C1 | 10/2011 | |
| WO | WO1993/004025 | 3/1993 | |
| WO | WO-9325507 A1 * | 12/1993 | ........... C07C 17/206 |
| WO | WO1996/011896 | 4/1996 | |
| WO | WO1997/005089 | 2/1997 | |
| WO | WO1998/010862 | 3/1998 | |
| WO | WO1998/033756 | 8/1998 | |
| WO | WO1998/037043 | 8/1998 | |
| WO | WO1999/062857 | 12/1999 | |
| WO | WO2004/018095 | 3/2004 | |
| WO | WO2005/012212 | 2/2005 | |
| WO | WO2005/023984 | 3/2005 | |
| WO | WO2005/037431 | 4/2005 | |
| WO | WO2005/037743 | 4/2005 | |
| WO | WO2005/037744 | 4/2005 | |
| WO | WO2005/042451 | 5/2005 | |
| WO | WO2005/108332 | 11/2005 | |
| WO | WO2005/108333 | 11/2005 | |
| WO | WO2005/108334 | 11/2005 | |
| WO | WO2006/106353 | 10/2006 | |
| WO | WO2007/056194 | 5/2007 | |
| WO | WO2007/079431 | 7/2007 | |
| WO | WO2007/079435 | 7/2007 | |
| WO | WO2007/145171 | 12/2007 | |
| WO | WO2008/002500 | 1/2008 | |
| WO | WO2008/008350 | 1/2008 | |
| WO | WO2008/030443 | 3/2008 | |
| WO | WO2008/040969 | 4/2008 | |
| WO | WO2008/054781 | 5/2008 | |
| WO | WO2008/054782 | 5/2008 | |
| WO | WO2008/075017 | 6/2008 | |
| WO | 2009/125200 A2 | 10/2009 | |
| WO | 2009125199 A2 | 10/2009 | |
| WO | 2009125201 A2 | 10/2009 | |
| WO | WO2009/140563 | 11/2009 | |
| WO | 2010026382 A2 | 3/2010 | |
| WO | 2010026383 A2 | 3/2010 | |
| WO | WO2011/140013 | 10/2011 | |
| WO | WO2011/140013 | 11/2011 | |
| WO | 2015/046345 | 4/2015 | |
| WO | WO 2018/046927 A1 | 3/2018 | |

OTHER PUBLICATIONS

Haszeldine et al., J. Chem. Soc., "Fluoro-olefins. Part II. Synthesis and Reactions of Some 3:3:3-trihalogenpropenes", 1953; pp. 3371-3378.

Sianesi et al., Fluoroolefins-Report 1 Cis and trans 1,2,3,3,3-pentafluoropropylene, Soc Montecatini Milan, Ann Chim (Rome), 55(8-9), 1965; pp. 850-861.

Banks et al., J. Fluorine Chem. vol. 82, 1997, pp. 171-174.

(56) References Cited

OTHER PUBLICATIONS

Buchner et al., Chemistry: A European Journal, vol. 4, 1998; pp. 1799-1809.
Joyce et al., J. Am. Chem. Soc. 1948; pp. 2529-2532.
Haszeldine et al., J. Chem. Soc. Perkin Trans. 1, 1979; pp. 1943-1947.
Haszeldine et al., J. Chem. Soc. 1970; pp. 414-421.
Haszeldine et al., J. Chem. Soc. Perkin Trans. 1, 1974; pp. 1303-1307.
Haszeldine et al., J. Chem. Soc. Perkin Trans. 1, 1976; pp. 2349-2353.
Meyer et al. Synthesis, 2000; pp. 1479-1490.
Atherton et al., J. Chem. Soc., 1971; pp. 366-371.
Boche et al., Chem. Ber., 1981; pp. 4005-4009 (no English Equivalent).
Baklouti et al., J. Fluorine Chem., 1981; pp. 181-190 (no English Equivalent).
M. B. Smith and J. March, Advanced Organic Chemistry, Reaction, Mechanisms, and Structure, 5th Edition, p. 1195; 2001.
Search Report pertaining to GB1615197.9; UK Patent Office dated Mar. 3, 2017.
Search Report cited in PCT/GB2017/052616 dated Dec. 22, 2017.
Written Opinion cited in PCT/GB2017/052616 dated Mar. 15, 2018.
He Yongjun, Synthesis And Catalytic Properties of Nano Oxides, Shaanxi Science & Technology Press, pp. 8-11.
Catalysts Studies on Fluorination from 2-chloro-3,3,3-trifluoropropenase to tetrafluoropropene (HFC-1234-yf, HFC-1234ze), Zunyun Xie, "Chinese Master's Theses Full-text Database Engineering Science and Technology I", No. 3, 2013, B014-232.
Solid Catalyst, Xiang Dehui, pp. 342-344, Chemical Industrial Press.
Design and Preparation of Solid Catalyst, Pan Lvrang, pp. 137-138, Nankai University Press.
Elementary Chemical Engineering, Wang Dingjin, pp. 337-339, Higher Education Press.
Office Action for corresponding Chinese application 201780061867.X, dated Jun. 17, 2021, 20 pgs.
English Translation of Office Action for corresponding Chinese application 201780061867.X, dated Jun. 17, 2021, 17 pgs.
Office Action for corresponding Chinese application 201780065320.7, dated Jul. 2, 2021, 21 pgs.
English Translation of Office Action for corresponding Chinese application 201780065320.7, dated Jul. 2, 2021, 16 pgs.
Notice of Opposition in Europe Application No. 17768203.6, dated Aug. 9, 2021, 32 pages.
Notice of Opposition in Europe Application No. 17768204.4, dated Aug. 9, 2021, 34 pages.
D1 Thesis Hadar Rotter, "Development & Testing the Nanostructured Transition Metal Oxides in Combustion of Volatile Organic Compounds," Mar. 2006, 9 pages.
D2 Rama Rao et al., "Influence of Method of Preparation on Pore Structure and Deydrogenation of Activity of Chromia Catalysts", Indian Journal of Chemistry, dated Aug. 1996, vol. 35 A, Aug. 1996, pp. 656-659, 4 pages.
D3 Petrov et al., "Effect of Chromium Content on the Properties of a Alumina-Chromia Catalyst in Tetrachlorethylene Hydrofluorination", AIP Conference Proceedings 1772.030009 (2016), (cited Oct. 13, 2016), 6 pages.
D4 (RU 2431524 C1) and D4a, Google machine translation of RU 2431524 C1, dated Oct. 20, 2011, 36 pages.*.
D5 (RU 2402378 C1) and D5a Google machine translation of RU 2402378 C1, dated Oct. 27, 2010, 36 pages.*.
D6 (RU 2322291 C1) and D6a Google machine translation of RU 2322291 C1, dated Apr. 20, 2008, 30 pages.*.
D10 Rouquerol et al. "Recommendations for the Characterization of Porous Solids (Technical Report)", Pure & Appl. Chem. Vol. 6 6, No. 8, 1994, pp. 1739-1758, International Union of Pure and Applied Chemistry, 20 pages.
D11 Thommes et al., Physisorption of Gases, with Special Reference to the Evaluation of Surface area and Pore Size Distribution (IUPAC Technical Report), Pure Appl. Chern. 2015, vol. 87, Nos. 9-10, pp. 1051-1069, Aug. 2015, 19 pages.

* cited by examiner

CATALYST AND PROCESS USING THE CATALYST FOR MANUFACTURING FLUORINATED HYDROCARBONS

Related Applications

This application is a U.S. National Phase entry under 35 U.S.C. § 371 of International Application No. PCT/GB2017/052616, filed Sep. 7, 2017, which claims the benefit of Great Britain Patent Application No. 1615197.9, filed Sep. 7, 2016, the contents of each of which are incorporated herein by reference in their entireties.

The invention relates to a catalyst, a method of preparing said catalyst and to a process that uses said catalyst. More particularly, the invention relates to a catalyst comprising one or more metal oxides and processes for using said catalyst in the addition or removal of halogen and halogen hydrides to/from compounds containing from 2 to 3 carbon atoms.

The listing or discussion of a prior published document in this specification should not necessarily be taken as an acknowledgement that the document is part of the state of the art or is common general knowledge.

Halocarbon-based compounds, particularly fluorocarbon-based compounds are currently used in a large number of commercial and industrial applications, such as propellants, blowing agents and heat transfer fluids. The interest in and use of fluorine-based compounds, particularly (hydro)fluoroolefins, as heat transfer fluids has increased as new refrigerants are sought.

(Hydro)haloalkenes such as hydrofluoropropenes can be conveniently prepared from corresponding hydro(halo)fluoroalkanes by dehydrohalogenation. The transformation can be effected thermally, i.e. by pyrolysis, catalytically, by contacting a hydro(halo)fluoroalkane with a catalyst under suitable conditions, or chemically, typically by contacting a hydro(halo)fluoroalkane with strong bases such as alkali metal hydroxides. For commercial operation, catalytic dehydrohalogenation is believed to be preferred.

The hydrofluoropropene 1,1,1,2,3-pentafluoropropene (HFO-1225ye), for example, can be prepared by contacting and dehydrofluorinating 1,1,1,2,3,3-hexafluoropropane in the gaseous state with trivalent chromium oxide or partially fluorinated trivalent chromium oxide, optionally in the presence of oxygen (see U.S. Pat. No. 5,679,875).

Similarly, fluorination and/or hydrofluorination steps are also common in the manufacturing processes of (hydro)fluoroalkenes. Such processes may be performed by contacting HF with one or more (hydro)haloalkenes or (hydro)haloalkanes, preferably in the presence of a catalyst.

Notwithstanding the above processes, catalytic reactions involving halocarbons have a number of problems in use, one of which is that industrial scale processes subject the catalysts to extreme temperatures and pressures, numerous regenerations and corrosive reagents. The skilled person will know that over the lifetime of an industrial catalyst the activity is steadily reduced and the catalyst must eventually be replaced in an expensive procedure.

There is therefore a need for catalysts with improved stability and comparable or improved activity relative to existing catalysts.

In a first aspect, the present invention provides a catalyst comprising one or more metal oxides and wherein the catalyst has a total pore volume of greater than 0.3 cm$^3$/g and the mean pore diameter is greater than or equal to 90 Å, wherein the total pore volume is measured by $N_2$ adsorption porosimetry and the mean pore diameter is measured by $N_2$ BET adsorption porosimetry.

The skilled person would appreciate that in catalysis in general, catalytic activity is understood to be proportional to the available surface area of the catalyst. It is to be expected that increasing the opportunity for the reagents to interact with the surface of the catalyst will improve the rate of conversion.

However, in contrast to established teaching, the present inventors have surprisingly found that increasing the pore volume and average pore diameter, which may inherently reduce a catalyst's surface area, increases both the stability and the activity of the catalyst.

Without wishing to be bound by theory, it is believed that this is a result of the increased mass transfer through the catalyst and that this effect is more pronounced for $C_3$ compounds than $C_2$ compounds. Also without wishing to be bound by theory, it is believed that the wider pore diameters of the present invention allow the catalyst in use to assume more quickly an effective pore structure for producing (hydro)haloalkenes such as hydrofluoropropenes.

The pore structure of solid porous materials can be determined by several methods, one of the most commonly used is the adsorption and desorption of $N_2$, based on the BET theory (Brunauer, Emmett and Teller) of the adsorption of multilayers of condensed gases onto solid surfaces, and the evaporation (desorption) of the adsorbed gas during desorption. Nitrogen is a common adsorbate for probing the micro and mesoporous regions. From the adsorption and desorption isotherms, the following can be calculated:

BET surface area from the adsorption of a monolayer of $N_2$, total pore volume taken from the amount of nitrogen adsorbed at P/P°=0.99 and average pore diameters can be determined using different calculations either based on the BET theory or that of BJH (Barrett, Joyner and Halenda), either from the adsorption or desorption data.

Preferably, the total pore volume of the catalyst is equal to or greater than 0.35 cm$^3$/g or 0.4 cm$^3$/g, such as 0.45 cm$^3$/g, 0.5 cm$^3$/g, 0.55 cm$^3$/g or even 0.6 cm$^3$/g when measured by $N_2$ adsorption porosimetry.

Preferably, the average pore width of the catalyst is greater than or equal to 100 Å, e.g. greater than or equal to 110 Å or greater than or equal to 120 Å when measured by $N_2$ BET adsorption porosimetry.

Preferably, the average pore width of the catalyst is greater than or equal to 130 Å, e.g. greater than or equal to 140 Å, greater than or equal to 150 Å or greater than or equal to 170 Å when measured by $N_2$ BJH adsorption porosimetry.

Preferably, the average pore width of the catalyst is greater than or equal to 90 Å, e.g. greater than or equal to 100 Å, greater than or equal to 110 Å or greater than or equal to 120 Å when measured by $N_2$ BJH desorption porosimetry.

Preferably, the catalyst is provided in the form of a pellet or pellets comprising a plurality of catalyst particles. Such catalyst particles may be pressed together, for example under load, to form the pellets.

The pellets may comprise one or more further materials. For example, the pellets may include graphite, preferably in an amount of from about 0.5 wt % to about 10 wt %, e.g. from about 1 wt % to about 5 wt %.

Preferably, the pellets have a longest dimension from about 1 mm to about 100 mm. In some embodiments, the pellets may have a longest dimension of about 1 mm to about 10 mm, for example from about 3 mm to about 5 mm.

The catalyst may be supported or unsupported. Typically, the metal in the metal oxide catalyst is one or more of any metal which forms a metal (oxy)fluoride which has Lewis acid character. Examples are metals selected from Li, Na, K, Ca, Mg, Cs, Al, Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La and Ce. Preferably, the metal is a transition metal and even more preferably is chromium.

The metal oxide catalyst used in the process of the invention may contain at least one additional metal or compound thereof. This additional metal or compound thereof can also be referred to as a promoter. In one embodiment, at least one additional metal is selected from Li, Na, K, Ca, Mg, Cs, Sc, Al, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La, Ce and mixtures thereof. Preferably, the at least one additional metal is selected from Li, Na, K, Ca, Mg, Cs, Cr, Zr, Nb, Pd, Ta, Zn, V, Mo, Ni, Co and mixtures thereof, even more preferably the additional metal is zinc.

Advantageously, the catalyst may be a zinc/chromia catalyst. By the term "zinc/chromia catalyst" we mean that the metal oxide catalyst comprises chromium or a compound of chromium and zinc or a compound of zinc.

The total amount of the zinc or a compound of zinc present in the zinc/chromia catalysts of the invention is typically from about 0.01 wt % to about 25 wt %, preferably 0.1 wt % to about 25 wt %, conveniently 0.01 wt % to 6 wt % zinc, and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst.

Preferably, the catalyst comprises at least 80 wt % (for example at least 85 wt %, at least 90 wt %, at least 92 wt %, at least 93 wt %, at least 94 wt %, at least 95 wt % or at least 96 wt %) chromia.

In some embodiments, the catalyst may be in fluorinated form. For example, the catalyst may have been fluorinated by treatment with HF at elevated temperature.

Advantageously, the catalysts of the present invention are unused, i.e. new. By 'unused' we mean that the catalyst possesses the total pore volume and average pore diameter, as specified above, before it has been contacted with any reagents or put under any pre-reaction conditions and/or the catalyst has not previously been used for catalysing a reaction or regenerated.

The present invention also provides a method of preparing a catalyst, said method comprising the steps of:
a) preparing a metal salt solution and a hydroxide solution;
b) combining the solutions at a pH of greater than 7.5 in order to precipitate the metal hydroxide(s);
c) drying the precipitated metal hydroxides;
d) calcining the metal hydroxide(s) to form the metal oxide(s).

Preferably, the metal salt comprises a nitrate salt such as a hydroxide nitrate salt. In preferred embodiments, the metal salt comprises chromium, and may comprise a chromium nitrate salt such as $Cr(OH)(NO_3)_2$. The hydroxide solution may comprise ammonium hydroxide ($NH_4OH$). Advantageously, step b) is carried out at a pH of greater than 8. Preferably, step b) is carried out at a pH of greater than or equal to 8.1, 8.2, 8.3; 8.4 or 8.5.

In some embodiments, the metal salt solution is provided at a concentration of from about 1 mol/l to about 10 mol/l, for example from about 2 mol/l to about 8 mol/l, e.g. from about 3 mol/l to about 7 mol/l or from about 4 mol/l to about 6 mol/l.

In some embodiments, the hydroxide solution is provided at a concentration of from 1 mol/l to about 10 mol/l, for example from about 2 mol/l to about 8 mol/l, e.g. from about 3 mol/l to about 7 mol/l or from about 4 mol/l to about 6 mol/l.

Preferably, step (b) is performed by combining the solutions in a body of solvent, such as water. Alternative solvents may include alcohols, glycols, water mixtures and other polar solvents.

Preferably, step b) is carried out at a substantially constant temperature, such as from 0 to 50° C., preferably from 10 to 30° C.

Preferably, step (b) is performed while agitating the combined solutions. Such agitation may be provided by known suitable means such as impellers, jet mixer, recirculation pumps and the like.

The precipitate formed during step (b) preferably comprises particles having average longest dimensions of from about 5 μm to about 20 μm, e.g. from about 7 μm to about 15 μm or from about 8 μm to about 13 μm, for example around 10 μm. Such dimensions are according to measurement by focused beam reflectance measurement.

Preferably, step (c) includes removing liquid from the slurry of metal hydroxide precipitate(s) to produce a wet cake, for example by filtration or centrifugal action. Such filtration may include the application of a pressure differential across the or a filtration membrane. The cake may be washed prior to any drying or calcining, preferably by exposure to water (e.g. deionised water) or aqueous alkali (such as ammonium hydroxide).

Preferably step (c) includes removing liquid, e.g. residual liquid, from the wet metal hydroxide(s) cake by exposing it to elevated temperature. Such elevated temperature may be, for example, between 50° C. and 200° C. and more preferably may be between 80° C. and 150° C., e.g. around 90° C. to around 120° C. The precipitate is preferably exposed to the elevated temperature for at least 15 mins, e.g. at least 30 mins or at least 1 hr. In certain embodiments, the precipitate may be subject to elevated temperature for over 6 hr or over 12 hr.

It is also preferred that step (d) includes a step of calcining the metal hydroxide, preferably after liquid removal and/or drying. Such a calcining step may include heating the metal hydroxides to a temperature between around 200° C. and around 550° C., for example between around 250° C. and around 500° C., e.g. around 300° C. to around 400° C. Such a calcining step may have a duration of from around 5 mins to around 12 hrs. It is particularly preferred to perform the calcination for a sufficient period to produce a catalyst having a TGA loss on ignition (LOI) of less than around 15%, for example less than around 12% or less than around 10%, for example around 8%, when heating to 400° C.

The method preferably comprises combining the calcined metal oxide with graphite to provide a catalyst composition comprising around 0.1 wt % to around 10 wt % graphite. In preferred embodiments, the composition so formed may comprise around 0.5 wt % to around 5 wt % graphite. It is most preferred that the composition so formed comprises around 1 wt')/0 to around 3 wt % graphite.

In preferred embodiments, the metal oxide and/or catalyst composition may be pressed to form catalyst pellets. The pressing may take place under a load of around 1 to 10 tonnes, e.g. around 5 tonnes. The pellets so formed may have a longest dimension from about 1 mm to about 100 mm. In some embodiments, the pellets may have a longest dimension of about 1 mm to about 10 mm, for example from about 3 mm to about 5 mm.

In embodiment further aspect of the invention, there is provided a process for fluorinating a $C_{2-3}$ hydrohalocarbon species, comprising contacting the species with a catalyst according to the invention. This is typically carried out in the presence of HF. For the avoidance of doubt, the term $C_{2-3}$ hydrohalocarbon includes saturated or unsaturated compounds with a two or three carbon chain and containing one or more atoms of hydrogen and a halogen (F, Cl, Br, I). In preferred embodiments, the hydrohalocarbon species comprises a $C_3$ hydrohalocarbon species.

An example of such a process comprises contacting trichloroethylene with the catalyst in the presence of HF to produce 1,1,1,2-tetrafluoroethane (134a), the conversion of 1,1,1,2,3-pentachloropropane (240 db) to 2-chloro-3,3,3-trifluoropropene (1233 xf), the conversion of 1233 xf to 2,3,3,3-tetrafluoropropene (1234 yf) and/or 1,1,1,2,2-pentfluoropropane (245 cb), the conversion of 1,1,1,3-tetrachloropropane (250fb) to 3,3,3-trifluoropropene (1243zf), or the conversion of 2,3-dichloro-1,1,1-trifluoropropane (243 db) to 1233 xf and/or 1234 yf.

In another aspect of the invention, there is provided a process for dehydrohalogenating a $C_{2-3}$ hydrohalocarbon species (preferably a $C_3$ hydrohalocarbon species), comprising contacting the species with a catalyst, such as contacting a hydro(halo)fluoropropane with the catalyst to produce a fluoropropene, preferably a tetrafluoropropene (1234) such as 1234ze ((E) or (Z)) or 1234 yf. Advantageously, this may include the conversion of 245 cb and/or 1,1,1,2,3-pentafluoropropane (245 eb) to 2,3,3,3-tetrafluoropropene (1234 yf) and/or 1,3,3,3-tetrafluoropropene (1234ze), the conversion of 1,1,1,3,3-pentafluoropropane (245fa) to 1234ze or the conversion of 1-chloro-1,3,3,3-tetrafluoropropane to 1-chloro-3,3,3-trifluoropropene (1233zd) or 1234ze.

In a further aspect of the invention, there is provided a process for eliminating HF or from a saturated $C_{2-3}$ hydrohalocarbon species (preferably a $C_3$ hydrohalocarbon species), comprising contacting the species with a catalyst according to the invention.

In a further aspect of the invention, there is provided a process for adding HF to an unsaturated $C_{2-3}$ hydrohalocarbon species (preferably a $C_3$ hydrohalocarbon species), comprising contacting the species with a catalyst according to the invention.

The claimed processes may be conducted in the liquid or the vapour phase but are preferably conducted in the vapour phase. The process may be carried out at atmospheric, sub- or super atmospheric pressure, typically at from 0 to about 30 bara, preferably from about 1 to about 20 bara, such as 15 bara.

Typically, the vapour phase process of the invention is carried out a temperature of from about 100° C. to about 500° C. (e.g. from about 150° C. to about 500° C. or about 100 to about 450° C.). Preferably, the process is conducted at a temperature of from about 150° C. to about 450° C., such as from about 150° C. to about 400° C., e.g. from about 175° C. to about 300° C. Lower temperatures may also be used in the conversion of 250fb to 1243zf, such as from about 150° C. to about 350° C., e.g. from about 150° C. to about 300° C. or from about 150° C. to about 250° C.

The processes typically employ a molar ratio of HF:organics of from about 1:1 to about 100:1, such as from about 3:1 to about 50:1, e.g. from about 4:1 to about 30:1 or about 5:1 or 6:1 to about 20:1 or 30:1.

The reaction time for the process generally is from about 1 second to about 100 hours, preferably from about 10 seconds to about 50 hours, such as from about 1 minute to about 10 or 20 hours. In a continuous process, typical contact times of the catalyst with the reagents are from about 1 to about 1000 seconds, such from about 1 to about 500 seconds or about 1 to about 300 seconds or about 1 to about 50, 100 or 200 seconds.

The present invention will now be illustrated by the following non-limiting Examples, illustrated by the following drawings.

EXAMPLES

Figure 1:
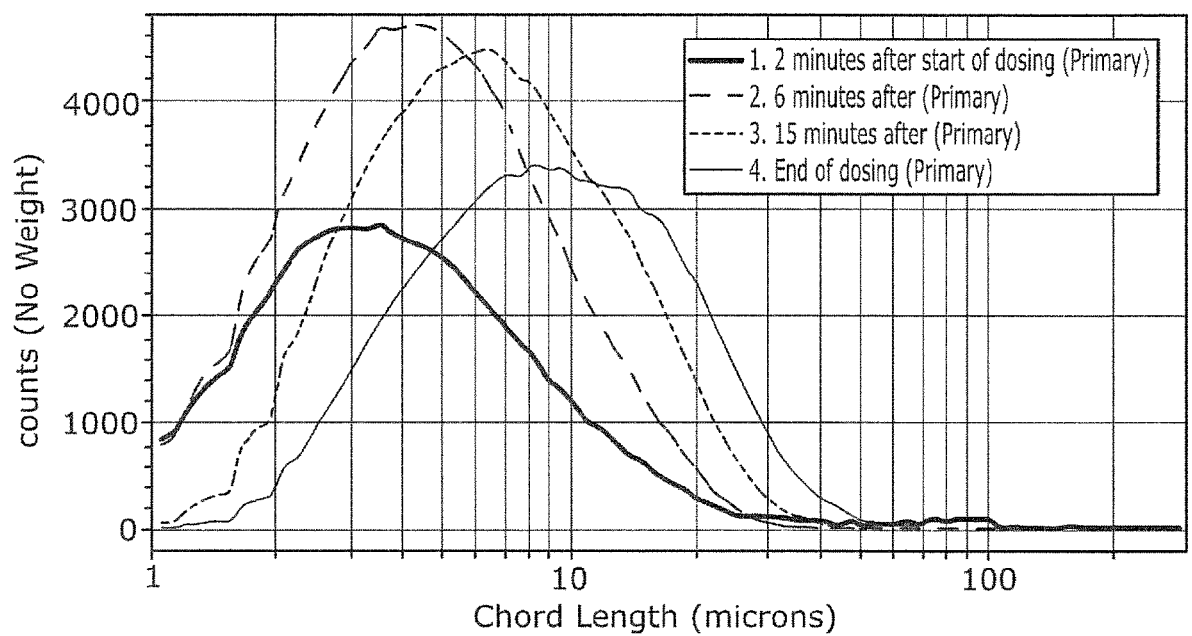
FIG. 1 shows a plot of the particle size distribution at temporal points during the reaction of Comparative Example 8, unweighted to emphasise smaller particles.

Catalysts of examples 1 to 7 were produced by the following method:

500 mL deionised water heel was added to a 1.7 L jacketed glass vessel, fitted with an overflow, overhead stirrer, pH probe and thermocouple and cooled to 15° C. The stirrer was actuated at 500 rpm, save for in example 5, where it was turned at 250 rpm.

$Zn(NO_3)_2 \cdot 6H_2O$ (19.03 g) was dissolved into a solution of $Cr(NO_3)_2(OH)_{(aq)}$ (500 g) in a 600 mL beaker. In another beaker, 500 g 17% $NH_4OH$ solution was provided.

The metal and ammonia solutions were pumped into the chilled water at 5 ml/min. Precipitation of a green/blue solid occurs immediately. The pH of the mixture was monitored and the reactant flow rates adjusted to maintain the target pH for each example as shown in Table 1, below. The reaction was run until all of the metal solution was added.

The slurry was filtered under vacuum until a filter cake formed then washed four times with de-ionised water ("a" examples) or dilute aqueous ammonia solution ("b" examples).

The filter cake was then dried at 105° C. overnight in a standard oven, followed by calcining under flowing nitrogen (200 ml/min) at 300° C. for 12 hours to produce 6.5%

ZnO/Cr$_2$O$_3$, the heating rate on the chamber furnace being set to 2° C./min. The percentage mass loss was on calcination was noted.

2 wt % graphite was blended with the cooled, calcined catalyst precursor in a waring blender, and the resultant mixture was sieved to <250 μm. The sieved mixture was formed into pellets under a load of 5 tonne in a 32 mm pellet die, 3 g per pellet.

The pellets were then ground to mesh size 0.5-1.4 mm for catalyst testing. Surface area, pore volumes and sizes were measured by N$_2$ adsorption/desorption porosimetry. Zn content was measured by X-ray fluorescence spectroscopy. The results are shown in Table 1, alongside results for Comparative Example 1, a chromia catalyst having a specified surface area of 160 to 200 m$^2$/g and pore volume of greater than 0.22 cm$^3$/g.

production of 133a and 134a from each was measured. The temperatures and yields across the reactors were monitored.

The organic feed was then turned off and with 30 ml/min HF flowing over the catalyst the reactor temperatures were ramped to 490° C. at 40° C./hr this was held for ten hours and cooled to 350° C. Trichloroethylene was then provided as above. This process was repeated for a stress temperature of 514° C. and, for some examples 522° C.

The activity and stability results are presented as a comparison to the results for Comparative Example 1, a commercial catalyst tested under the same conditions.

Activity is determined according to the calculation

Activity=50−(S2−RT)

where S2 is the predicted reaction temperature to obtain 10% 134a yield at Stress Temperature 2 and where RT is 287.5° C.

TABLE 1

| Example | Actual pH | Water Heel/g | Stirrer speed/rpm | Temp/° C. | Slurry Wash Sol$^n$ | BET SA (m$^2$/g) | Pore Volume (cm$^3$/g) @ 0.99P/P° | BET Ads Average pore width (Å) | BJH Ads Average pore width (Å) | BJH Des Average pore width (Å) |
|---|---|---|---|---|---|---|---|---|---|---|
| CE1 | | | | | | 180 | 0.282 | 63 | 107 | 65 |
| CE2a | 7.2-7.3 | 500 | 500 | 15-17 | DI H$_2$O | 171 | 0.259 | 60 | 112 | 63 |
| CE2b | | | | | NH$_4$OH | 125 | 0.221 | 71 | 124 | 72 |
| 3a | 7.5-8.1 | 500 | 500 | 15-16 | DI H$_2$O | 125 | 0.327 | 105 | 147 | 102 |
| 3b | | | | | NH$_4$OH | 127 | 0.382 | 121 | 169 | 116 |
| 4 | 8.3 | 500 | 500 | 15-16 | DI H$_2$O | 129 | 0.442 | 137 | 184 | 129 |
| 5a | 8.3-8.4 | 500 | 500 | 17-18 | DI H$_2$O | 111 | 0.449 | 162 | 190 | 143 |
| 5b | | | | | NH$_4$OH | 111 | 0.464 | 167 | 195 | 147 |
| 6a | 8.3-8.4 | 500 | 500 | 15-16 | DI H$_2$O | 172 | 0.506 | 118 | 192 | 127 |
| 6b | | | | | NH$_4$OH | 138 | 0.447 | 129 | 189 | 131 |
| 7a | 8.2-8.4 | 500 | 500 | 15-17 | DI H$_2$O | 132 | 0.512 | 155 | 198 | 148 |
| 7b | | | | | NH$_4$OH | 151 | 0.508 | 135 | 191 | 138 |

The data clearly shows that a significant raising of the pore volume of a precipitated catalyst is provided when the pH of precipitation is raised.

The pelleted catalysts were tested for their efficacy in converting trichloroethylene to 134a. An atmospheric pressure screening rig was equipped with four reactor tubes, each with independent HF, organic and nitrogen feeds. The organic feed system was charged with trichloroethylene. Each reactor was charged with 2 g of catalyst with a particle size in the range 0.5-1.4 mm. Initially the nitrogen flow (60 ml/min) was directed to the reactor inlet and the catalysts dried at 250° C. for 1 hour.

Following the catalyst drying operation HF vapour was fed to each reactor at a flow of 30 ml/min, diluted with nitrogen (60 ml/min), and passed over the catalysts at 250° C. for approximately 30 minutes until HF was observed in the reactor off gases. At this point the nitrogen flows (reduced to 30 ml/min) were redirected to the reactor exits. The catalysts were then exposed to the HF:N$_2$ (30:5-ml/min) stream for a further hour at 250° C. before the temperatures were ramped to 450° C. at 40° C. per hour. These temperatures were held for ten hours.

The reactors were initially cooled to 350° C. and trichloroethylene was fed over the catalysts by sparging nitrogen (8 ml/min) through liquid trichloroethylene at 10° C. This gave a 0.5 ml/min flow of trichloroethylene gas. The catalysts were allowed to equilibrate in the HF:trichloroethylene:N$_2$ (30:0.5:10-ml/min) gas stream for about 2 hours before the reactor temperatures were reduced to 300° C. The catalysts were again allowed to equilibrate for about 1 hour before the Stability is determined according to the calculation Stability=50−(S3−RT)

where S3 is the predicted reaction temperature to obtain 10% 134a yield at Stress Temperature 3 and where RT is 287.5° C.

The results are shown in Table 2, below.

TABLE 2

| Example | Precipitation pH | Predicted Reaction Temp to Obtain 10% 134a Yield | | | | Activity | Stability |
|---|---|---|---|---|---|---|---|
| | | Stress 1 450° C. | Stress 2 490° C. | Stress 3 514° C. | Stress 4 522° C. | | |
| CE 1 | | 288.90 | 287.50 | 295.50 | 318.90 | 50 | 42 |
| CE2a | 7.2-7.3 | 296.00 | 297.04 | 308.61 | — | 40.5 | 28.9 |
| CE2b | | 307.64 | 292.58 | 301.11 | — | 44.9 | 36.4 |
| 3a | 7.5-8.1 | 287.22 | 284.37 | 291.35 | — | 53.1 | 46.2 |
| 3b | | — | 279.71 | 281.90 | — | 57.8 | 55.6 |
| 4 | 8.3 | 284.70 | 286.04 | 284.79 | 304.00 | 51.5 | 52.7 |
| 5a | 8.3-8.4 | 288.46 | 286.80 | 290.93 | 308.82 | 50.7 | 46.6 |
| 5b | | 286.78 | 284.96 | 289.00 | 308.18 | 52.5 | 48.5 |
| 6a | 8.3-8.4 | 282.16 | 279.32 | 283.17 | 301.29 | 58.2 | 54.3 |
| 6b | | 281.68 | 285.05 | 288.90 | 306.29 | 52.5 | 48.6 |
| 7a | 8.2-8.4 | 281.48 | 282.46 | 288.26 | 303.83 | 55.0 | 49.2 |
| 7b | | 282.35 | 278.32 | 282.84 | 297.90 | 59.2 | 54.7 |

The results show a clear correlation between increased pore volume and width and increased stability and activity over prior art catalysts. This activity appears to be sustained even where there is a decrease in surface area compared to the commercial catalyst.

Examples 8 and 9 and Comparative Examples 10 and 11

Catalysts were prepared substantially according to the method of Examples 1 to 7, adapted as described below with reference to Table 3.

A Mettler Toledo Optimax automated laboratory reactor was fitted with Focused Beam Reflective Measurement (FBRM) G400 14 mm probe with overhead stirring and charged with 500 ml a deionised water heel.

The metal solution was pumped to the reactor at 5 ml/min. 17% Ammonium hydroxide solution was also added at 5 ml/min. The pH was closely monitored and the flow rates of the reactants altered to maintain the target pH. The reaction was run until 300 g of the metal solution was added. The particle size of the precipitate was monitored during the reaction using the FBRM G400 probe.

TABLE 3

| Example | Metal solution | Target pH |
|---|---|---|
| CE8 | 300 g Chromium hydroxide nitrate (~10% Cr) | pH 7 |
| 9 | 300 g Chromium hydroxide nitrate (~10% Cr) | pH 8.5 |
| CE10 | 300 g Chromium hydroxide nitrate (~10% Cr) + 11.4 g Zn(NO$_3$)$_2$·6H$_2$O | pH 7 |
| 11 | 300 g Chromium hydroxide nitrate (~10% Cr) + 11.4 g Zn(NO$_3$)$_2$·6H$_2$O | pH 8.5 |

The resulting slurries were vacuum filtered and washed three times with de-ionised water. The filter cake was dried at 110° C. then, calcined under flowing nitrogen (200 ml/min) at 300° C. for 12 hours to produce Cr$_2$O$_3$ and 6.5% ZnO/Cr$_2$O$_3$. This was milled and mixed with 2% graphite before being pelleted at 5 tonne.

Comparative Example 8

Figure 2:
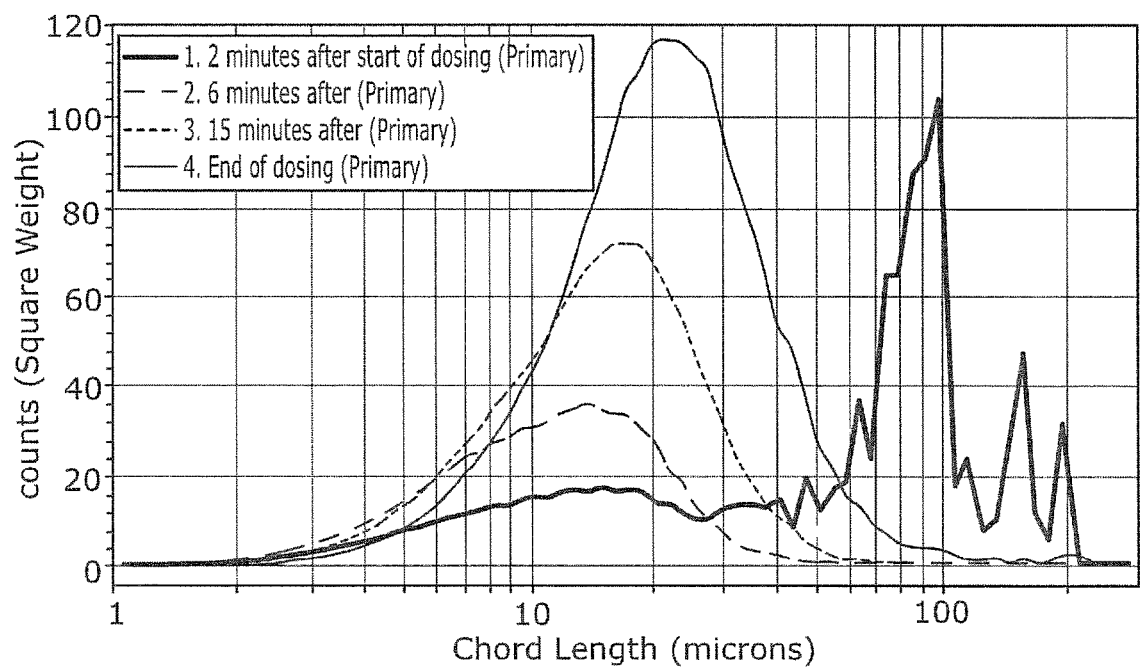
FIG. 2 shows a plot of the particle size distribution at temporal points during the reaction of Comparative Example 8, weighted to emphasise larger particles.

FIGS. 1 and 2 and table 4 show the measured particle size distribution 2, 6 and 15 minutes after the start of dosing and once dosing is complete. 2 minutes after the start there are mostly very small particles, but also a few large particles present. These large particles are not present 6 minutes after the start of dosing, by which time the small particle population is at its greatest. Thereafter, the distribution shows a gradual shift to large size.

TABLE 4

| Statistic | 2 min. | 6 min. | 15 min. | End |
|---|---|---|---|---|
| Median No Wt | 3.7 | 4.3 | 6.2 | 8.7 |
| Mean Sq Wt | 67.8 | 12.6 | 16.6 | 24.4 |
| Counts <5 μm | 45949 | 66179 | 42031 | 21046 |
| Counts 5-8 μm | 12838 | 25269 | 27048 | 19349 |
| Counts 8-25 μm | 10920 | 22241 | 37550 | 42532 |
| Counts 25-300 μm | 1493 | 357 | 1576 | 5377 |

Example 9

Figure 3:
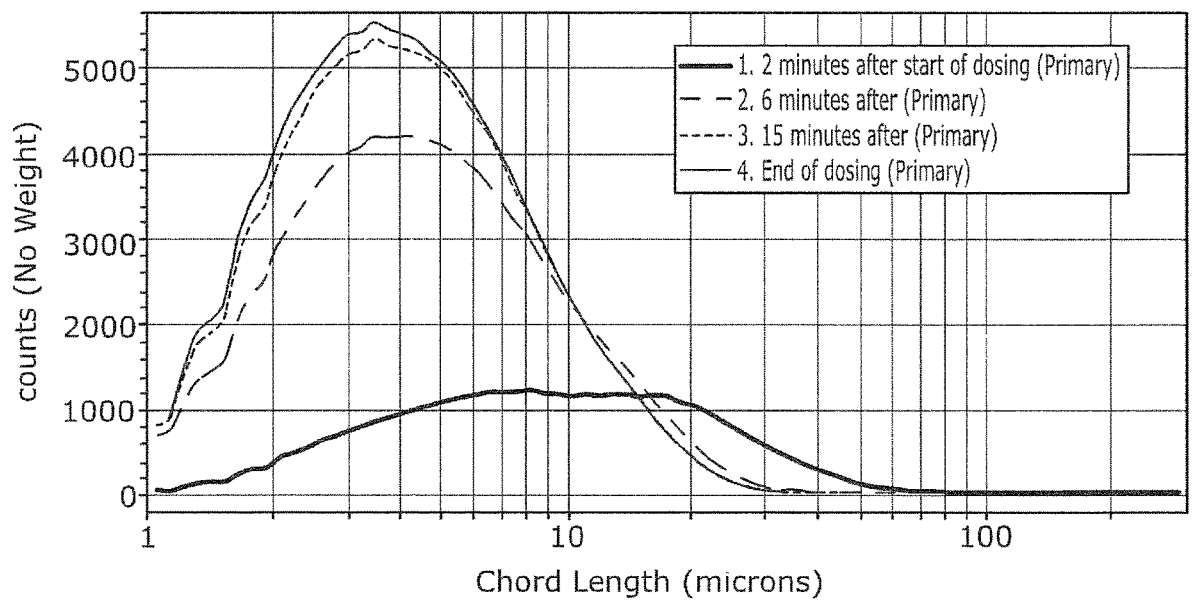
FIG. 3 shows a plot of the particle size distribution at temporal points during the reaction of Example 9, unweighted to emphasise smaller particles.
Figure 4:
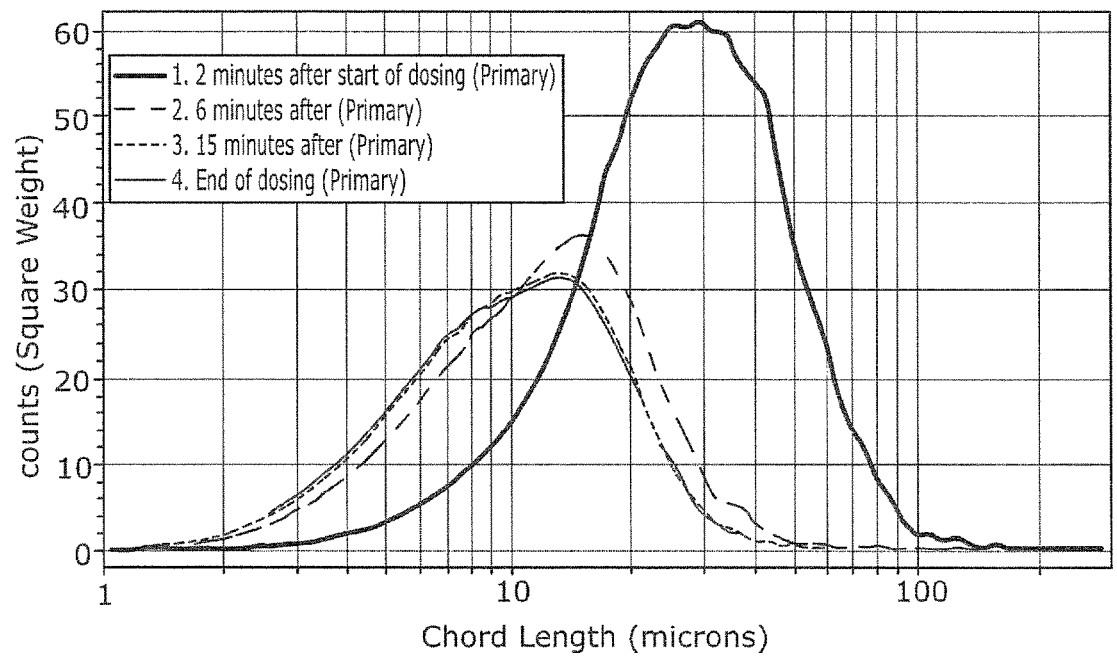
FIG. 4 shows a plot of the particle size distribution at temporal points during the reaction of Example 9, weighted to emphasise larger particles.

FIGS. 3 and 4 and table 5 show the measured particle size distribution 2, 6 and 15 minutes after the start of dosing and once dosing is complete. 2 minutes after the start there are mostly large particles present. But by 6 minutes, the number of large particles has reduced, and the number of small particles has increased significantly. The particle system shows very little change for the final 15 minutes of dosing.

TABLE 5

| Statistic | 2 min. | 6 min. | 15 min. | End |
|---|---|---|---|---|
| Median No Wt | 8.6 | 4.3 | 4.0 | 3.9 |
| Mean Sq Wt | 30.1 | 13.4 | 11.8 | 11.5 |
| Counts <5 | 10732 | 60239 | 77458 | 81366 |
| Counts 5-8 | 7135 | 22430 | 26103 | 26522 |
| Counts 8-25 | 16259 | 21560 | 20603 | 20341 |
| Counts 25-300 | 3858 | 460 | 233 | 228 |

Comparative Example 10

Figure 5:
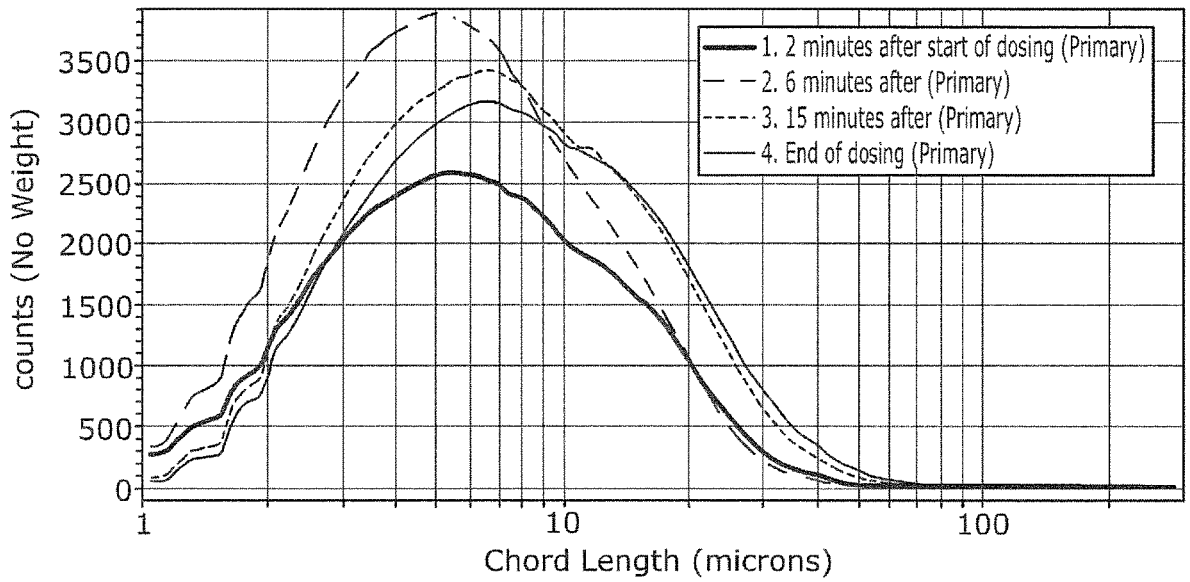
FIG. 5 shows a plot of the particle size distribution at temporal points during the reaction of Comparative Example 10, unweighted to emphasise smaller particles.
Figure 6:
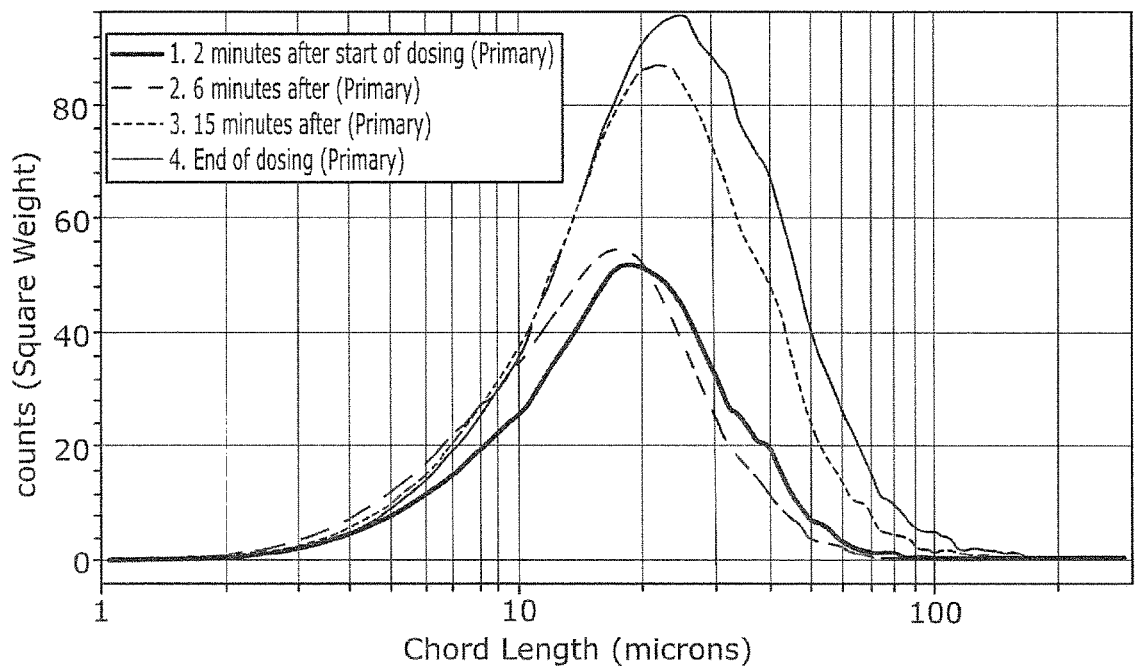
FIG. 6 shows a plot of the particle size distribution at temporal points during the reaction of Comparative Example 10, weighted to emphasise larger particles.

FIGS. 5 and 6 and table 6 show the measured particle size distribution 2, 6 and 15 minutes after the start of dosing and once dosing is complete. 2 minutes after the start there are mostly small particles present which increase in number as 6 minutes is reached. After that, the population of those small particles gradually decreases, and the number of larger particles increases.

TABLE 6

| Statistic | 2 min. | 6 min. | 15 min. | End |
|---|---|---|---|---|
| Median No Wt | 5.9 | 5.3 | 6.8 | 7.3 |
| Mean Sq Wt | 19.7 | 17.0 | 23.4 | 26.7 |
| Counts <5 μm | 29859 | 46790 | 32806 | 28764 |
| Counts 5-8 μm | 15510 | 22717 | 20755 | 19240 |
| Counts 8-25 μm | 23382 | 28384 | 35207 | 35337 |
| Counts 25-300 μm | 1798 | 1346 | 4113 | 5314 |

Example 11

Figure 7:
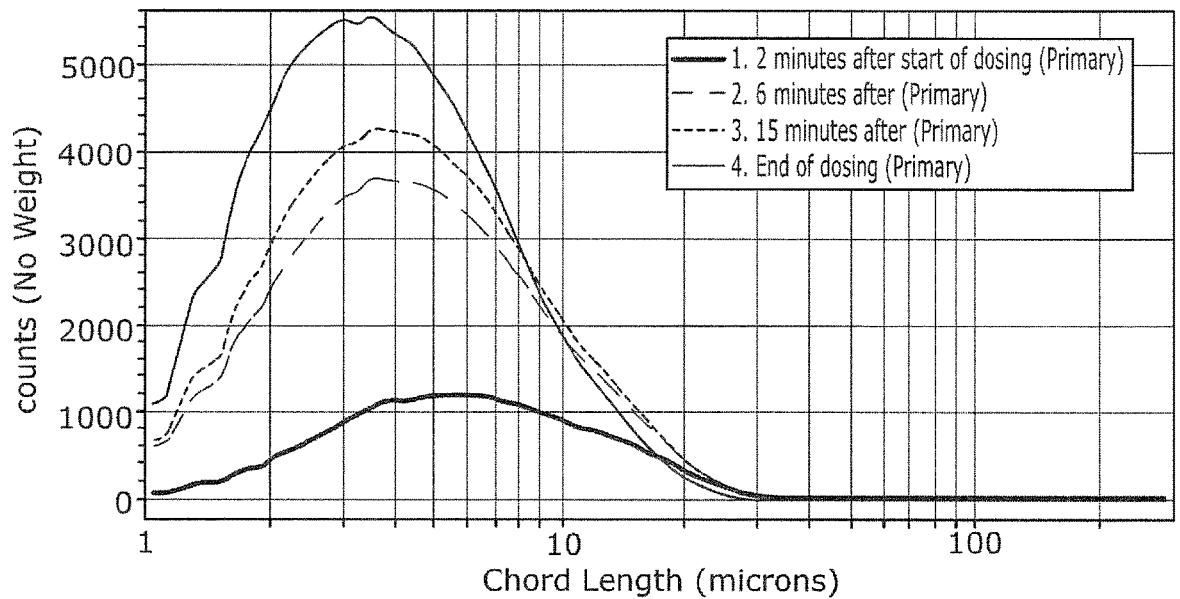
FIG. 7 shows a plot of the particle size distribution at temporal points during the reaction of Example 11, unweighted to emphasise smaller particles.
Figure 8:
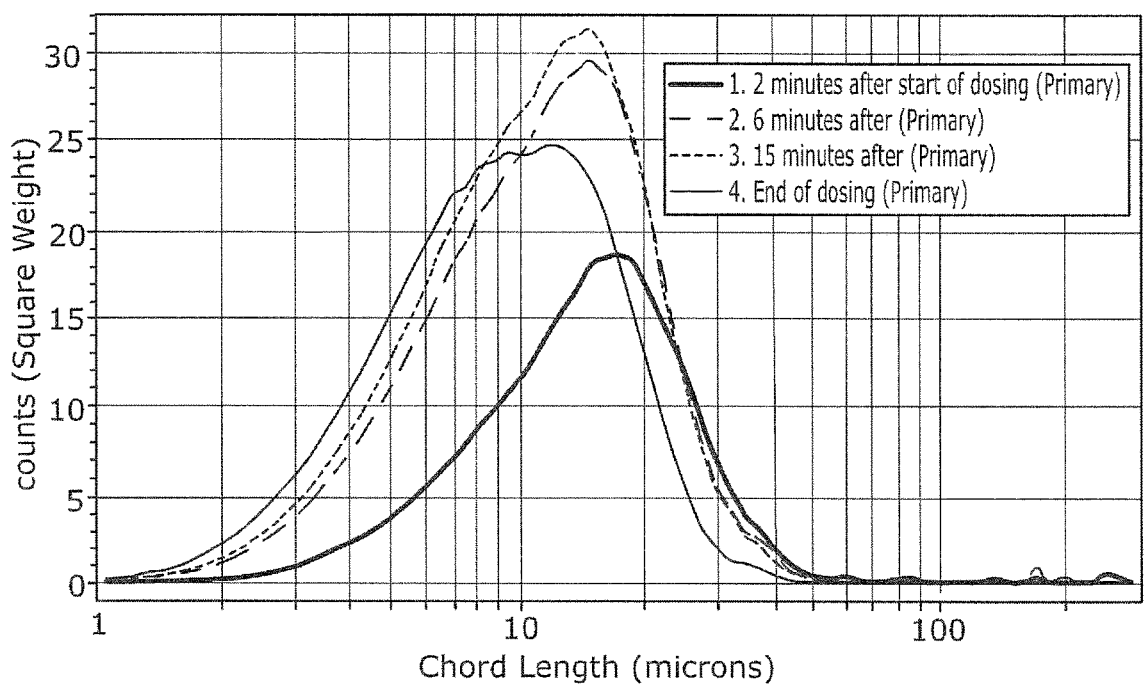
FIG. 8 shows a plot of the particle size distribution at temporal points during the reaction of Example 11, weighted to emphasise larger particles.

FIGS. 7 and 8 and table 7 show the measured particle size distribution 2, 6 and 15 minutes after the start of dosing and once dosing is complete. The distributions show that over the course of dosing, there is a gradual increase in the numbers of smaller particles. For the final 15 minutes of dosing, there is a decrease in the number of larger particles.

TABLE 7

| Statistic | 2 min. | 6 min. | 15 min. | End |
|---|---|---|---|---|
| Median No Wt | 5.7 | 4.3 | 4.1 | 3.6 |
| Mean Sq Wt | 16.8 | 13.2 | 12.4 | 10.4 |
| Counts <5 μm | 12933 | 52574 | 61877 | 87005 |
| Counts 5-8 μm | 7197 | 19203 | 21662 | 24208 |
| Counts 8-25 μm | 9559 | 17822 | 19193 | 16282 |
| Counts 25-300 μm | 352 | 297 | 284 | 112 |

Figure 9:
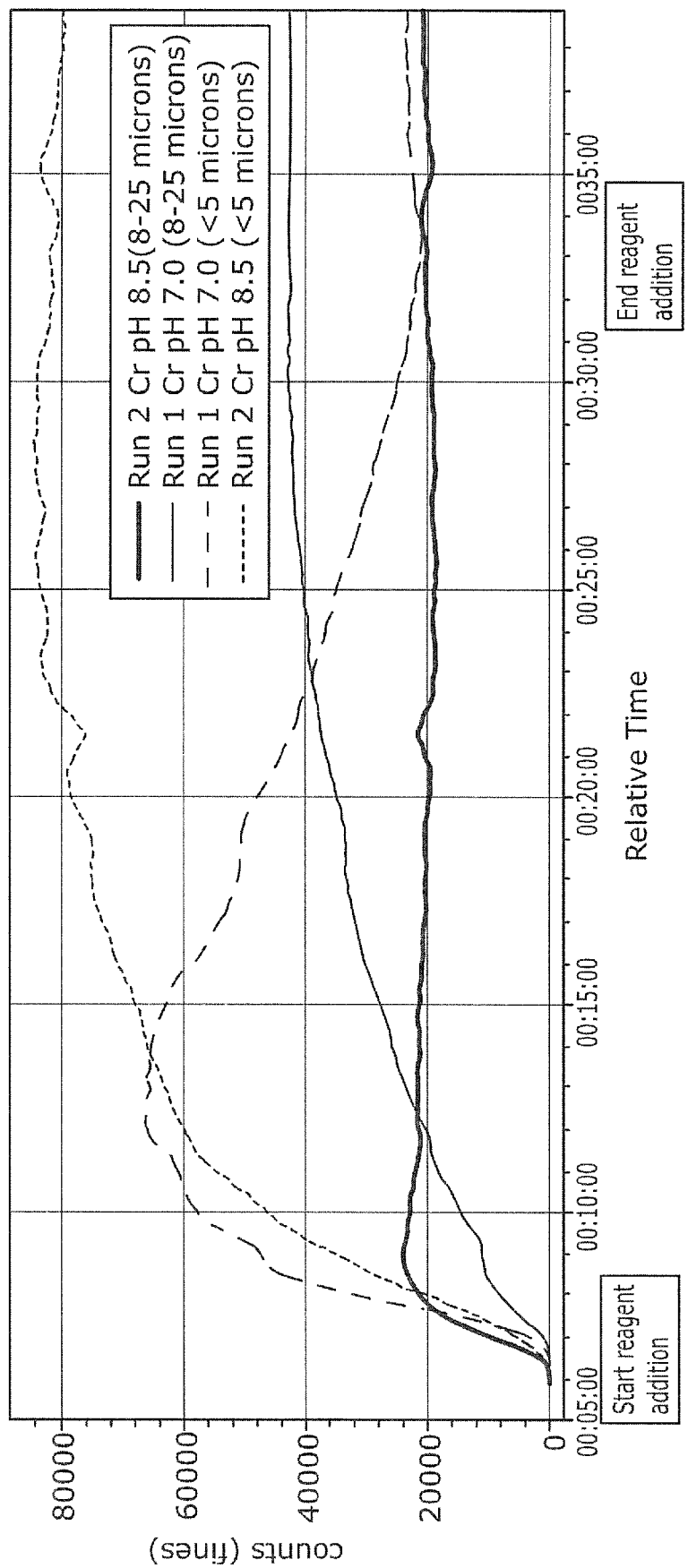
FIG. 9 shows a plot of the presence of fine particles during the reactions of Examples and Comparative Examples 8 to 11.

FIG. 9 shows the real time data collection for the fines count (less than 5 μm and 8 μm to 25 μm) for Comparative Examples 8 and Example 9. From this it was possible to see instantly the effect of any flow disturbances or pH fluctuations. It also demonstrates that leaving the final slurry to stir for an extended period had no effect on particle size or distribution.

Figure 10:
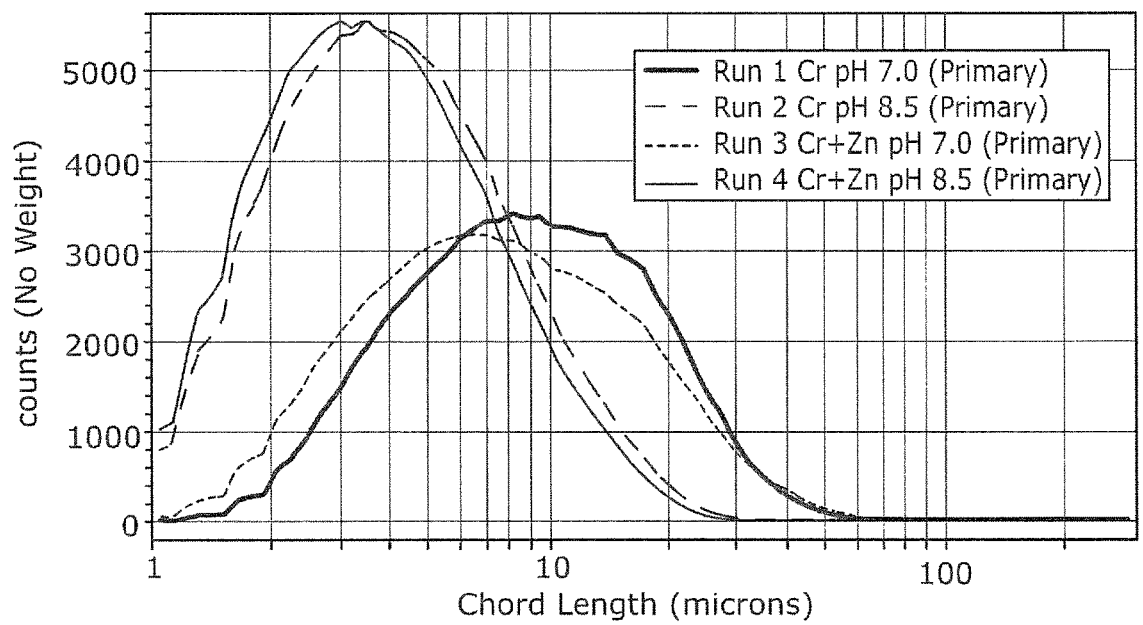
FIG. 10 shows a plot of the particle size distributions at completion of the reactions of Examples and Comparative Examples 8 to 11 unweighted to emphasise smaller particles.
Figure 11:
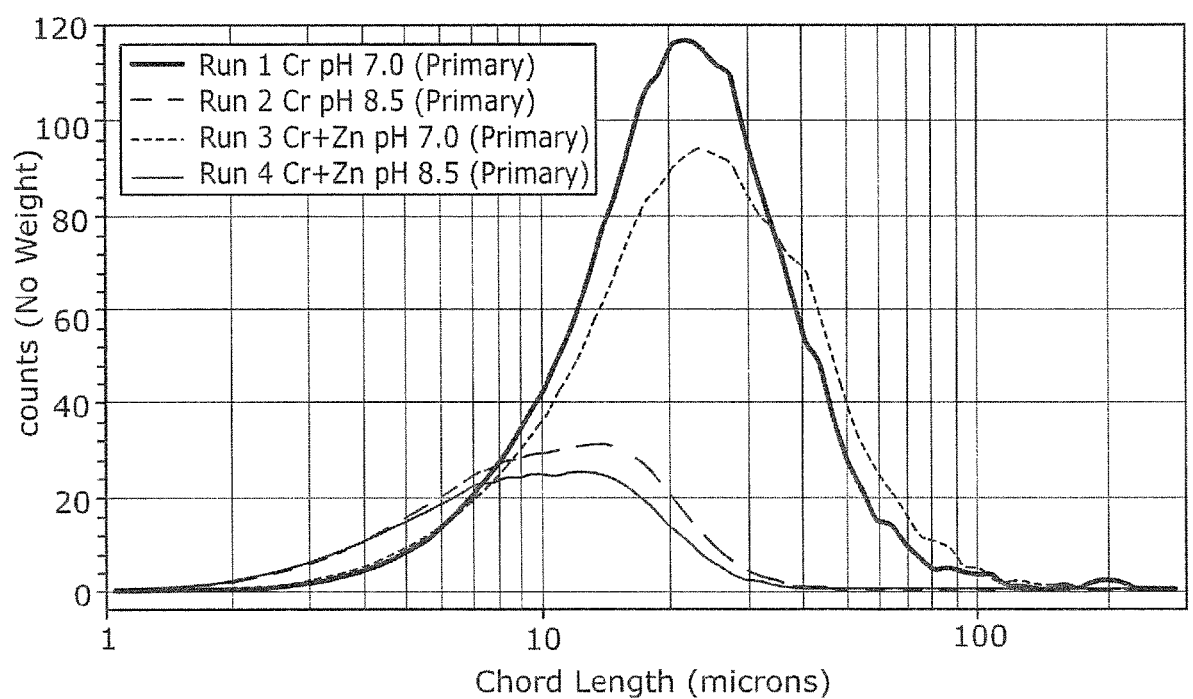
FIG. 11 shows a plot of the particle size distributions at completion of the reactions of Examples and Comparative Examples 8 to 11 weighted to emphasise larger particles.

A comparison of the final particle size distributions of the slurries is shown in FIGS. 10 and 11 and Table 8. The results clearly show that increasing the pH of precipitation has a significant effect on the particle population and size. Both runs at pH 8.5 have a smaller average size than those at pH 7.0, and more small particles. Changing the metal composition also has an effect but much smaller in scale. Both runs with zinc show a slightly smaller average size compared to the chromium only counterparts.

The resulting dried, calcined and pelleted catalysts were tested by $N_2$ adsorption/desorption porosimetry to determine surface area, total pore volume and average pore diameter. The results are shown in Table 8, below.

TABLE 8

| Example | pH | Mean particle length (slurry) Microns | BET $m^2/g$ | Pore volume $cm^3/g$ @P/P°0.99 | BJH Ads Average pore diameter Å |
|---|---|---|---|---|---|
| CE8 | 7 | 24.5 | 243.75 | 0.21 | 51.2 |
| 9 | 8.5 | 11.4 | 207.69 | 0.64 | 189.2 |
| CE10 | 7 | 26.5 | 241.00 | 0.45 | 100.1 |
| 11 | 8.5 | 10.5 | 200.98 | 0.72 | 206.7 |

It is clear that the catalysts of Comparative Examples 8 and 10 (prepared at pH 7) had a larger particle size in the slurry and a larger BET surface area and a smaller pore diameter and volume. In contrast, the catalysts of Examples 9 and 11 (prepared at pH 8.5) had a smaller particle size in the slurry which resulted in a smaller BET surface area and a larger pore diameter and volume.

The catalysts of Examples 9 and 11 and Comparative Examples 8 and 10 were subjected to the same performance testing as Examples 1 to 7. The results are shown in Table 9 below.

TABLE 9

| | | | Predicted temp to Obtain 10% 134a Yield | | |
|---|---|---|---|---|---|
| Example | Activity | Stability | Stress 1 450° C. | Stress 2 490° C. | Stress 3 514° C. |
| CE8 | 42.4 | 34.33 | 285.03 | 295.10 | 303.17 |
| 9 | 50.27 | 48.38 | 287.36 | 287.23 | 289.12 |
| CE10 | 45.89 | 46.93 | 295.66 | 291.61 | 290.57 |
| 11 | 59.08 | 46.27 | 274.38 | 278.42 | 291.23 |

These results show improved stability of the catalysts of Examples 9 and 11 over the comparative Examples 8 and 10. This demonstrates that the favouring of larger pore sizes, larger pore volumes and/or smaller precipitated particle diameter upon precipitation over BET surface area provides for improved performance in the catalysts. These parameters may be controlled by controlling the pH of precipitation.

Preferences and options for a given aspect, feature or parameter of the invention should, unless the context indicates otherwise, be regarded as having been disclosed in combination with any and all preferences and options for all other aspects, features and parameters of the invention.

Example 12 and Comparative Example 13

In Example 12, chromia catalyst pellets were made according to the following method. 500 mL deionised water heel was added to a 1.7 L jacketed glass vessel, fitted with an overflow, overhead stirrer, pH probe and thermocouple and cooled to 15° C. The stirrer was actuated at 500 rpm A solution of $Cr(NO_3)_2(OH)_{(aq)}$ (1036 g) was measured into a 2000 mL beaker. In another beaker, 599 g 17% $NH_4OH$ solution was provided.

The metal and ammonia solutions were pumped into the chilled water at 5 ml/min. Precipitation of a green/blue solid occurs immediately. The pH of the mixture was monitored and the reactant flow rates adjusted to maintain the target of pH 8.5. The reaction was run until all of the metal solution was added.

The chromium hydroxide slurry was divided into two portions and filtered separately under vacuum until a filter cake formed then each washed three times with de-ionised water (3×500 mL). The resulting filter cakes were combined, then divided into four. One portion of cake was then dried at 80° C. for 3-days in a standard oven, followed by calcining under flowing nitrogen (200 ml/min) at 300° C. for 12 hours to produce $Cr_2O_3$, the heating rate on the chamber furnace being set to 2° C./min. The percentage mass loss was on calcination was noted.

2 wt % graphite was blended with the cooled, calcined catalyst precursor in a waring blender, and the resultant mixture was sieved to <250 µm. The sieved mixture was formed into pellets under a load of 5 tonne in a 32 mm pellet die, 3 g per pellet.

The pellets were then ground to mesh size 0.5-1.4 mm for catalyst testing. Surface area, pore volumes and sizes were measured by $N_2$ adsorption/desorption porosimetry.

Production of 1234 yf from 243 db

The performance of the catalyst of Example 12 was tested for the production of 1234 yf from the fluorination of 243 db by contact with HF and compared to the performance for a commercially available chromia catalyst containing no promoter. The pore volumes and diameters for each catalyst were also tested.

An atmospheric pressure screening rig was equipped with four reactor tubes, each with independent HF, organic and nitrogen feeds. The organic feed system was charged with 243 db. Each reactor was charged with 2 ml of catalyst with a particle size in the range 0.5 1.4 mm. Initially the nitrogen flow (60 ml/min) was directed to the reactor inlet and the catalysts dried at 200° C. for 2 h.

Following the catalyst drying operation HF vapour was fed to each reactor at a flow of 30 ml/min, diluted with nitrogen (60 ml/min), and passed over the catalysts at 300° C. for approximately 60 minutes until HF was observed in the reactor off gases. At this point the nitrogen flows (reduced to 30 ml/min) were redirected to the reactor exits. The reactor temperatures were ramped to 360° C. at 40° C. per hour. These temperatures were held for ten hours.

The reactors were cooled to 350° C. and 243 db was fed over the catalysts by sparging nitrogen (4-6 ml/min) through liquid 243 db at 10° C. This gave a 0.5-1 ml/min flow of 243 db gas. The catalysts were allowed to equilibrate in the HF:243 db:$N_2$ (30:0.5-1.0:4-6 ml/min) gas stream for about 1 h before sampling reactor off-gas into a glass burette with DI water for GC analysis. The results are shown in Table 10 below.

TABLE 10

| Example | Catalyst | Temperature/° C. | 243db conversion % | 1243yf selectivity % | Pore volume pre test (N$_2$ absorption)/ cm$^3$/g | Pore volume post test (N$_2$ absorption)/cm$^3$/g | Average BJH ads pore diameter pre test/Å | Average BJH ads pore diameter post test/Å |
|---|---|---|---|---|---|---|---|---|
| 12 | Cr$_2$O$_3$ | 350 | 100 | 40.26 | 0.44 | 0.34 | 147 | 261 |
| CE13 | Cr$_2$O$_3$ | 350 | 100 | 17.95 | 0.28 | 0.21 | 101 | 167 |

The results show a clear improvement in selectivity for 1234 yf when the catalyst of the present invention is utilised. Furthermore, the results show that the catalyst of the invention shows significant pore widening once used, which without wishing to be bound by any theory, may amplify the effect of providing a high pore volume and average pore diameter in the unused catalyst.

Example 14

500 mL deionised water heel was added to a 1.7 L jacketed glass vessel, fitted with an overflow, overhead stirrer, pH probe and thermocouple and cooled to 15° C. The stirrer was actuated at 430 rpm. A solution of Cr(NO$_3$)$_2$(OH)$_{(aq)}$ (332 g) was measured into a 600 mL beaker and 17% NH$_4$OH solution (476 g) into another beaker.

The metal and ammonia solutions were pumped into the chilled water at 5 ml/min. Precipitation of a green/blue solid occurs immediately. The pH of the mixture was monitored and the reactant flow rates adjusted to maintain the target pH 8.5. The reaction was run until all of the solutions were added.

The chromium hydroxide slurry was filtered under vacuum until a filter cake formed then washed with deionised water (3×500 mL). The filter cake was then dried at 105° C. overnight in a standard oven, followed by calcining under flowing nitrogen (200 ml/min) at 300° C. for 12 hours to produce Cr$_2$O$_3$, the heating rate on the chamber furnace being set to 2° C./min.

2 wt % graphite was blended with the cooled, calcined catalyst precursor in a waring blender, and the resultant mixture was sieved to <250 μm. The sieved mixture was formed into pellets under a load of 5 tonne in a 32 mm pellet die, 3 g per pellet. The pellets were then ground to mesh size 0.5-1.4 mm for catalyst testing.

Analysis showed a BET surface area of 211 m$^2$/g, a Pore Volume @0.99 P/P° of 0.731 cm$^3$/g and average BJH adsorption pore diameter of 199 Å.

Example 15

A further catalyst was produced according to the method of Examples 1 to 7, targeting a pH of 8 to 8.5 during production.

Production of 1234 yf and 245 cb from 1233 xf

The performance of the catalyst of Examples 12, 14 and 15 was tested for the production of 1234 yf and 245 cb from the fluorination of 1233 xf by contact with HF. The results were compared to those of a commercially available chromia catalyst (Comparative Example 16).

Each catalyst (3 mL, 0.5-1.4 mm) was charged to an 0.5" OD Inconel 625 reactor supported by Inconel mesh. The catalysts were dried at 250° C. under 60 ml/min flowing nitrogen for at least 2 hours prior to pre-fluorination. HF vapour flowing at 30 ml/min was then passed over the catalyst along with 30 ml/min nitrogen at 250° C. for one hour. The nitrogen was then directed to the reactor exit leaving neat HF passing over the catalyst. The temperature was slowly ramped to 380° C. and held for 10 hours. The temperature was then reduced to 350° C. and the HF flow reduced to 25 mL/min. A co-feed of 1233 xf (2-chloro-3,3,3-trifluoropropene) was fed by its own vapour pressure and the flow controlled to 1 mL/min through an orifice plate. Reactor off-gas was sampled periodically from 0.5 to 7 h of continuous running, into deionised water and analysed by GC to determine reaction progress. Results are shown in Table 11.

TABLE 11

| Catalyst Example | Pore Volume @0.99P/P° (cm$^3$/g) | Average. BJH Ads Pore Diameter (Å) | Activity 1233xf Conv. (%) | Product Yield 1234yf mol (%) | Product Yield 245cb mol (%) | Conv. Decay rate (Stability) k (h$^{-1}$) | Conv. Half-life (Stability) t$_{0.5}$ (h) | Conv. Half-life (Stability) t$_{0.5}$ (h · g$^{-1}$) |
|---|---|---|---|---|---|---|---|---|
| CE16 | 0.284 | 101 | 27.8 | 18.8 | 5.4 | 0.13 | 5.6 | 2 |
| 12 | 0.440 | 147 | 82.8 | 43.6 | 13.9 | 0.04 | 16.5 | 9.7 |
| 14 | 0.731 | 199 | 84.3 | 45.4 | 14.3 | 0.12 | 5.8 | 4.5 |
| 15 | 0.606 | 205 | 70.9 | 50.8 | 13.6 | 0.13 | 5.5 | 3.4 |

It appears from the results shown in Table 11 that increasing the pore volume and average pore diameter of the pure chromia catalysts relative to the catalyst of Comparative Example 16 led to an increase in the catalyst activity and product yield. There was also an improvement in catalyst stability.

Production of 1234 yf from 245 cb

The performance of the catalyst of Examples 12, 14 and 15 was tested for the production of 1234 yf from the dehydrofluorination of 245 cb. The results were compared to those of a commercially available chromia catalyst (Comparative Example 17).

Each catalyst (3 mL, 0.5-1.4 mm) was charged to an 0.5" OD Inconel 625 reactor supported by Inconel mesh. The catalysts were dried at 250° C. under 60 ml/min flowing nitrogen for at least 2 hours prior to pre-fluorination. HF vapour flowing at 30 mL/min was then passed over the catalyst along with 30 mL/min nitrogen at 250° C. for one hour. The nitrogen was then directed to the reactor exit leaving neat HF passing over the catalyst. The temperature was slowly ramped to 380° C. and held for 10 hours. The temperature was then reduced to 250° C. and the HF flow reduced to 25 mL/min. A co-feed of 245 cb (1,1,1,2,3-pentafluoropropane) vapour was fed by sparging nitrogen (1 ml/min) through the liquid at 9° C. and resulting in a 245 eb flow of 1 mL/min. Reactor off-gas was sampled periodically from 0.5 to 7 h of continuous running into deionised water and analysed by GC to determine reaction progress. Results are shown in Table 12.

TABLE 12

| Catalyst Example | Mass/g | Pore Volume @0.99P/P° (cm³/g) | Average. BJH Ads Pore Diameter (Å) | Activity 245cb Conversion (%) |
|---|---|---|---|---|
| CE17 | 2.7 | 0.284 | 101 | 78.5 |
| 12 | 1.7 | 0.440 | 147 | 82.7 |
| 14 | 1.4 | 0.731 | 199 | 81.7 |
| 15 | 1.7 | 0.606 | 205 | 79.3 |

It appears from the data in Table 12 that the catalyst activity of the high pore volume and large pore catalysts was higher than that of the catalyst of Comparative Example 17. The Zn promoted catalyst of Example 15 also increased the yield of 1234 yf. All of the catalysts were equally stable.

Production of 1234 yf from 245 eb

The performance of the catalyst of Example 12 was tested for the production of 1234 yf and 245 cb from the dehydrofluorination of 245 eb. The results were compared to those of a commercially available chromia catalyst (Comparative Example 16).

Each catalyst (3 mL, 0.5-1.4 mm) was charged to an 0.5" OD Inconel 625 reactor supported by Inconel mesh. The catalysts were dried at 250° C. under 60 mL/min flowing nitrogen for at least 2 hours prior to pre-fluorination. HF vapour flowing at 30 ml/min was then passed over the catalyst along with 30 mL/min nitrogen at 250° C. for one hour. The nitrogen was then directed to the reactor exit leaving neat HF passing over the catalyst. The temperature was slowly ramped to 380° C. and held for 10 hours. The temperature was then reduced to 250° C. and the HF flow reduced to 25 mL/min. A co-feed of 245 eb (1,1,1,2,3-pentafluoropropane) vapour was fed by sparging nitrogen (1 mUnnin) through the liquid at 9° C. and resulting in a 245 eb flow of 1 mL/min. Reactor off-gas was sampled periodically from 0.5 to 7 h of continuous running into deionised water and analysed by GC to determine reaction progress. The results are shown in Table 13.

TABLE 13

| Catalyst Example | Mass/g | Pore Volume @0.99P/P° (cm³/g) | Average. BJH Ads Pore Diameter (Å) | Activity 245eb Conversion (%) | Rate of increase in activity 245eb Conversion gain (%/h) | Yield 1234yf mol (%) |
|---|---|---|---|---|---|---|
| CE16 | 2.7 | 0.284 | 101 | 18.7 | 0.5 | 15.3 |
| 12 | 1.7 | 0.440 | 147 | 36.5 | 6.8 | 22.1 |

It appears from the results in Table 13 that the catalyst activity and 1234 yf yield was higher over the high pore volume/large pore catalyst than it was over the catalyst of Comparative Example 16. In addition the activity of the high pore volume/large pore catalyst steadily increased over time and produced a higher yield of 1234 yf.

Preferences and options for a given aspect, feature or parameter of the invention should, unless the context indicates otherwise, be regarded as having been disclosed in combination with any and all preferences and options for all other aspects, features and parameters of the invention.

The invention claimed is:

1. A fluorination catalyst comprising one or more metal oxides, wherein the catalyst does not comprise Ni, Pd, Al, or Pt, wherein the catalyst has a total pore volume equal to or greater than 0.4 cm³/g and a mean pore diameter greater than or equal to 90 Å, wherein the pore volume is measured using $N_2$ adsorption porosimetry and the mean pore diameter is measured using $N_2$ BET adsorption porosimetry, and wherein at least 80 wt % of the one or more metal oxides has an atomic ratio of oxygen to metal of 1.5.

2. The catalyst according to claim 1, wherein the mean pore diameter of the catalyst is greater than or equal to 100 Å when measured by $N_2$ BET adsorption porosimetry.

3. The catalyst according to claim 1, wherein the mean pore diameter of the catalyst is greater than or equal to 130 Å when measured by $N_2$ BJH adsorption porosimetry.

4. The catalyst according to claim 1, wherein the mean pore diameter of the catalyst is greater than or equal to 90 Å when measured by $N_2$ BJH desorption porosimetry.

5. The catalyst according to claim 1 provided as a pellet or pellets comprising a plurality of catalyst particles.

6. The catalyst according to claim 5, wherein the pellet or pellets comprise graphite.

7. The catalyst according to claim 5, wherein the pellet or pellets have a longest dimension from about 1 mm to about 100 mm.

8. The catalyst according to claim 1, wherein the catalyst comprises a transition metal.

9. The catalyst according to claim 8, wherein the transition metal is chromium.

10. The catalyst according to claim 1, wherein the catalyst is unused.

11. A process for manufacturing a tetrafluoropropene comprising contacting a hydro(halo)propene with HF in the presence of the catalyst according to claim 10.

12. The process according to claim 11, wherein the hydro(halo)propene comprises a hydrochlorofluoropropene.

13. A process for eliminating HF from a saturated $C_{2-3}$ hydrohalocarbon species, comprising contacting the species with the catalyst according to claim 10.

14. A fluorinated catalyst according to claim 10.

15. The catalyst according to claim 1, wherein a metal in the catalyst is selected from the group consisting of Li, Na, K, Ca, Cs, Sc, Y, Ti, Zr, Hf, V, Nb, Ta, Cr, Mo, W, Mn, Re, Ru, Rh, Ir, Cu, Ag, Au, La, and Ce.

16. A method of preparing a catalyst as defined in claim 1, comprising the steps of:

a) preparing a metal salt solution and a hydroxide solution;
b) combining the solutions at a pH of greater than 8.0 in order to precipitate a metal hydroxide(s);
c) drying the precipitated metal hydroxide(s); and
d) calcining the metal hydroxide(s) to form the metal oxide(s).

17. The method according to claim 16, wherein step b) is carried out at a pH of greater than or equal to 8.5.

18. The method according to claim 16, wherein the metal salt comprises a nitrate salt.

19. The method according to claim 16, wherein the hydroxide solution comprises ammonium hydroxide ($NH_4OH$).

20. The method according to claim 16, wherein the metal salt solution is provided at a concentration of from about 1 mol/l to about 10 mol/l.

21. The method according to claim 16 wherein the hydroxide solution is provided at a concentration of from 1 mol/l to about 10 mol/l.

22. The method according to claim 16, wherein step (b) is performed by combining the solutions in a body of solvent.

23. The method according to claim 16, wherein step b) is carried out at a substantially constant temperature.

24. The method according to claim 16, wherein step (b) is performed while agitating the combined solutions.

25. The method according to claim 16, wherein the precipitate formed during step (b) comprises particles having average longest dimensions of from about 5 μm to about 20 μm.

26. The method according to claim 16, wherein step (c) comprises removing liquid from the precipitated metal hydroxide(s) to produce a wet cake.

27. The method according to claim 26, wherein the cake is washed prior to any drying or calcining.

28. The method according to claim 26, wherein step (c) comprises removing liquid from the wet metal hydroxide(s) cake by exposing it to elevated temperature.

29. The method according to claim 28, wherein the precipitate is exposed to the elevated temperature for at least 15 minutes.

30. The method according to claim 16, wherein step (d) comprises a step of calcining the metal hydroxide(s), after liquid removal and/or drying.

31. The method according to claim 16, wherein the calcining step comprises heating the metal hydroxide(s) to a temperature between about 200° C. and about 550° C.

32. The method according to claim 16, wherein the calcining step is performed for a sufficient period to produce a catalyst having a TGA loss on ignition (LOI) of less than about 15%.

33. The method according to claim 16 further comprising combining the calcined metal oxide(s) with graphite to provide a catalyst composition comprising about 0.1 wt % to about 10 wt % graphite.

34. The method according to claim 16, wherein the calcined metal oxide(s) and/or catalyst composition is pressed to form catalyst pellets.

35. The method according to claim 34, wherein the pressing takes place under a load of about 1 to 100 tonnes.

36. The method according to claim 35, wherein the pellets so formed have a longest dimension from about 1 mm to about 100 mm.

37. A process for fluorinating a $C_{2-3}$ hydrohalocarbon species, comprising contacting the species with the catalyst according to claim 1.

38. The process according to claim 37, comprising contacting trichloroethylene with the catalyst in the presence of HF to produce 1,1,1,2-tetrafluoroethane (134a).

39. The process according to claim 37 wherein the species is a $C_3$ hydrohalocarbon species.

40. The process according to claim 37, wherein the method is conducted in the vapour phase.

41. A process for dehydrohalogenating a $C_{2-3}$ hydrohalocarbon species, comprising contacting the species with the catalyst according to claim 1.

42. The process according to claim 41, comprising contacting a hydro(halo)fluoropropane with the catalyst to produce a fluoropropene.

43. The process according to claim 42, wherein the fluoropropene is a tetrafluoropropene (1234).

44. The process according to claim 43, wherein the hydro(halo)fluoropropane comprises a compound selected from the group consisting of: 1,1,1,2,3-pentafluoropropane, 1,1,1,2,2-pentafluoropropane and/or 1,1,1,3,3-pentafluoropropane.

45. The process according to claim 43, wherein the tetrafluoropropene comprises 1,3,3,3-tetrafluoropropene and/or 2,3,3,3-tetrafluoropropene.

46. A process for adding HF to an unsaturated $C_{2-3}$ hydrohalocarbon species, comprising contacting the species with the catalyst according to claim 1.

* * * * *